United States Patent [19]

Heller et al.

[11] 4,339,100
[45] Jul. 13, 1982

[54] ARRANGEMENT AT A STAND FOR AN OPTICAL OBSERVATION DEVICE

[75] Inventors: Rudolf Heller; Walter Schindler, both of Zurich, Switzerland

[73] Assignee: Contraves AG, Zürich, Switzerland

[21] Appl. No.: 167,538

[22] Filed: Jul. 10, 1980

[30] Foreign Application Priority Data

Jul. 24, 1979 [CH] Switzerland .......................... 6848/79

[51] Int. Cl.³ .......................... F16L 3/00; A47G 29/00
[52] U.S. Cl. .................................... 248/123.1; 350/85
[58] Field of Search ................... 248/123.1, 280.1, 325, 248/648, 665, 593, 292.1, 281.1; 350/85

[56] References Cited

U.S. PATENT DOCUMENTS

| | | | |
|---|---|---|---|
| 2,548,476 | 4/1951 | Horstmann | 248/281.1 |
| 2,967,458 | 1/1961 | Stone | 350/85 X |
| 3,475,075 | 10/1969 | Stone | 350/85 |
| 3,762,796 | 10/1973 | Heller | 350/85 |
| 3,790,249 | 2/1974 | Treace | 350/85 X |
| 3,809,454 | 5/1974 | Brambring | 350/84 |
| 3,887,267 | 6/1975 | Heller | 350/85 |
| 3,891,301 | 6/1975 | Heller | 350/85 |
| 4,167,302 | 9/1979 | Karasawa | 350/85 X |
| 4,241,891 | 12/1980 | Rudolph | 248/123.1 |

FOREIGN PATENT DOCUMENTS 548568 4/1974 Switzerland .

Primary Examiner—J. Franklin Foss
Attorney, Agent, or Firm—Werner W. Kleeman

[57] ABSTRACT

An arrangement at a stand for an optical observation device, especially for a surgical microscope, containing a stand which essentially comprises an upright column or stand at which there is pivotably mounted an arm member for pivotable movement about a horizontal axis. There are further provided a support arm, a number of rotary and brake bearings and a hinge parallelogram at which there is suspended the microscope or the like. At one end of the arm member or arm there is arranged a guide lever and at the other end a weighting disk as well as a brake bearing at which there is secured a rod carrying a counterweight. The guide lever and the rod are operatively connected with one another by means of a thrust rod extending parallel to the arm member. This arm member is arrestable and positionably fixable at the stand column by means of a bolt member insertable into the weighting disk and radially penetrating the column body. The support arm is arrestable and positionally fixable at the guide lever by means of an element insertable into the support arm and arranged at the guide lever.

6 Claims, 6 Drawing Figures

ARRANGEMENT AT A STAND FOR AN OPTICAL OBSERVATION DEVICE

CROSS-REFERENCE TO RELATED CASE

This application is related to our commonly assigned, copending U.S. application Ser. No. 06/167,540, filed July 10, 1980, entitled "AUXILIARY APPARATUS AT A STAND FOR AN OPTICAL OBSERVATION DEVICE".

BACKGROUND OF THE INVENTION

The present invention relates to a new and improved arrangement at a stand for an optical observation device.

Generally speaking, the arrangement of the present development is of the type comprising a stand having an upright or stand column, a pivotable arm mounted at the stand column and provided with a counterweight, a support arm, a plurality of rotary and brake bearings and a hinge parallelogram. The hinge parallelogram is structured such that at its front region it is capable of accommodating an optical observation device, in particular a surgical microscope.

Adjustable supports or stands for an optical observation instrument are well known to the art, as evidenced for instance by the commonly assigned U.S. Pat. Nos. 3,762,796, granted Oct. 2, 1973, 3,762,797, granted Oct. 2, 1973, 3,887,267, granted June 3, 1975 and 3,891,301, granted June 24, 1975.

In particular, in Swiss Pat. No. 548,568 and the corresponding U.S. Pat. No. 3,891,301 there is disclosed a support device for a surgical microscope, which is constructed as a stand and equipped with a number of rotary and brake bearings. With this prior art construction it is known to arrange at a stand or upright column a pivotable arm constructed as a balance and pivotable about a first horizontal axis. At the pivotable arm there is arranged to be displaceable and fixedly positionable a first balancing or compensation weight. At the upper region of the pivotable arm there is provided an intermediate element constructed as a balance beam, at which there is arranged at one side a hinge parallelogram structured for the reception and attachment of the surgical microscope and at the other side a further displaceably mounted balancing or compensation weight. This balancing or compensation weight is arranged to be cantilevered to such a degree and possesses a mass such that it corresponds to the weight of the suspended microscope. Such arrangement of the compensation or balancing weight at the pivotal arm and the intermediate element are particularly suitable for support devices of massive construction which are not subject to any spatial limitations.

SUMMARY OF THE INVENTION

Therefore, with the foregoing in mind it is a primary object of the present invention to provide at a support device of the previously mentioned type and which is constructed as a stand and serving for supporting a surgical microscope or other optical observation instrument, a space and weight-saving arrangement of the compensation or balancing weight.

A further significant object of the present invention aims at providing a new and improved arrangement at a stand for an optical observation device wherein the positional adjustment of the optical observation device can be carried out quickly, easily, in a most simple, reliable and rapid fashion, and with space-saving and weight-saving arrangement of a compensation weight for the optical observation device.

Now in order to implement these and still further objects of the invention, which will become more readily apparent as the description proceeds, the arrangement at a stand for an optical observation device as comtemplated by the invention is manifested by the features that at one end of the pivotable arm there is mounted a guide lever which is pivotable about a first horizontal axis and at the other end of the pivotable arm there is arranged a weight or weighing disk at a second horizontal axis as well as a rotary and brake bearing. A rod which carries the counterweight is secured to the brake bearing. This rod is oriented transversely with respect to the second horizontal axis and is essentially parallel to the guide lever. This rod is operatively connected with the guide lever by a thrust rod extending essentially parallel to the pivotal arm.

According to a further feature of the invention, in order to attain optimum use of the equipment and for realizing a certain mounting position of the stand, the pivotal arm together with the weight disk can be locked or arrested at the column body of the upright or stand column, and the support arm at which there is arranged the hinge parallelogram, can be locked or arrested at the guide lever. By means of the inventive arrangement of the balancing or compensation weight, it is possible in constrast to heretofore known support devices, to achieve the beneficial result that the construction of the support device is simplified and space-saving. Additionally, there can be obtained an exact movement of the freely adjustable, but positionally fixable microscope throughout a predetermined spatial region as concerns its position and orientation. A further simplification resides in the fact that by virtue of the inventive arresting of the support and pivotal elements there is readily accessible the microscope which is suspended at the hinge parallelogram and the same can be easily exchanged without having to resort to complicated measures and without the need for additional auxiliary aids.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
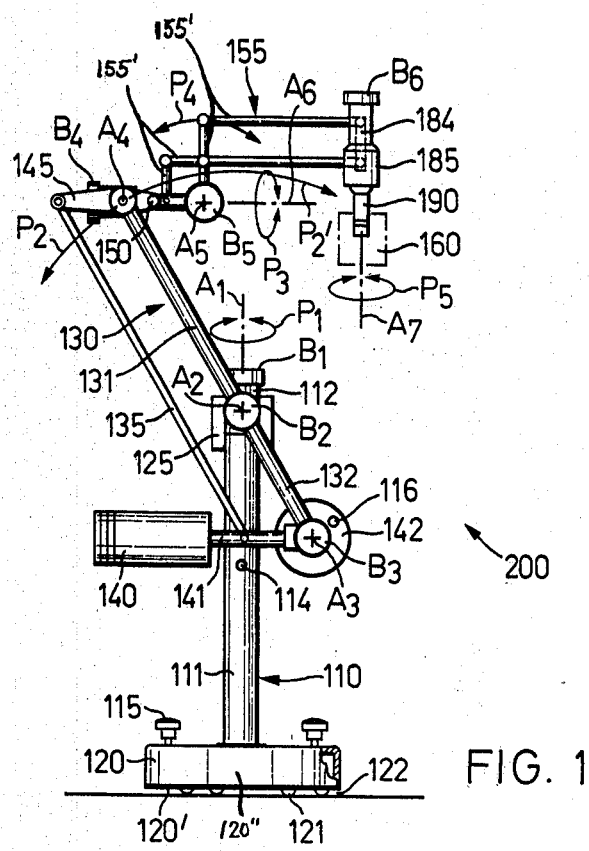
FIG. 1 is a perspective view of a stand equipped with the inventive arrangement of the pivotal, guide, support and movement elements.

Describing now the drawings, in FIG. 1 reference character 200 designates a mobile support device for optical observation devices or instruments, especially a surgical microscope by way of example and not limitation. The mobile support device 200 is constructed as a floor stand and essentially comprises a stand column or upright 110, a pivotable or pivotal arm 130 formed of two partial elements or pieces 131, 132, a support arm 147 and a hinge parallelogram 155 formed of a number of parallelogram elements, generally designated by reference character 155'. As explained in detail in our aforementioned copending application, the hinge parallelogram 155 is structured at its front end so that it can conveniently receive and have attached thereto the schematically illustrated optical observation device 160, here assumed to be a surgical microscope. The stand column or upright 110 essentially comprises a stand base or foot portion 120 which is mounted upon casters or rollers 121, a preferably tubular-shaped column body 111 and a head element or piece 112. The stand column 110 can be conveniently levelled and arrested at the supporting surface or floor by means of threaded bolts or screws 115 arranged at the stand base or foot portion 120.

The stand base or foot portion 120, shown partially in section in FIG. 1, is preferably structured to have a substantially bell-shaped configuration. The lower edge 120' of the encircling base ring or skirt 120" extends up to approximately the supporting surface or floor in order to provide improved standing stability of the entire stand 200. It has been found to be particularly advantageous to provide a spacing 122 between the floor and the lower edge 120' of the base ring or skirt 120" amounting to about 3–5 millimeters. The casters or rollers 121 as well as the threaded screws or bolts 115 are appropriately arranged in spaced relationship to one another in a certain geometric configuration at the stand base 120.

At the upper region of the column body 111 there is arranged the head element or piece 112 which is rotatable in the direction of the double-headed arrow $P_1$ about a vertical axis $A_1$ in relation to the fixedly positioned column body 111. At the head element 112 there is laterally secured a conventional brake bearing $B_2$. Attached at the brake bearing $B_2$ are both of the partial elements 131, 132 of the pivotal arm 130. This pivotal arm or arm member 130 is pivotable, on the one hand, about the horizontal axis $A_2$ of the brake bearing $B_2$ in the direction of the arrows $P_2$, $P_2'$ and, on the other hand, can be rotated in conjunction with the head element 112 about the vertical axis $A_1$ in the double-headed direction of the arrow $P_1$. The pivotable movement, as indicated by the arrows $P_2$, $P_2'$, can be manually braked essentially by the brake bearing $B_2$ and the rotatable movement $P_1$ by the brake bearing $B_1$.

Figure 4:
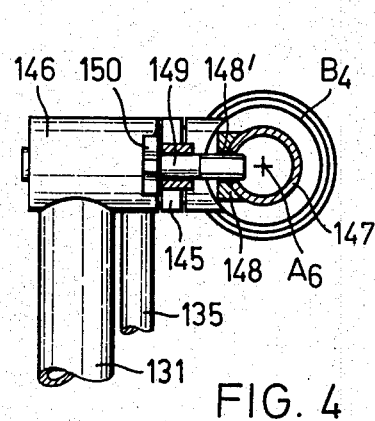
FIG. 4 is a sectional view of the arrangement of FIG. 3, taken substantially along the line IV–IV thereof.
Figure 3:
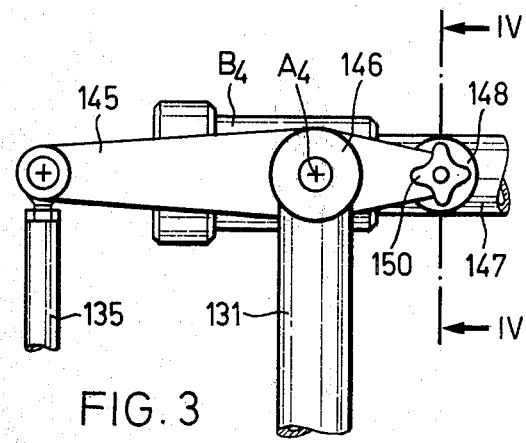
FIG. 3 is a fragmentary detail view, on an enlarged scale, of the upper part of the pivotal, guide, support and movement elements.

FIGS. 3 and 4 illustrate in an enlarged view the upper portion of the stand 200. In particular there will be recognized the partial element or member 131 of the pivotal arm 130 and the support arm 147 which is for instance substantially tubular-shaped. The partial element 131 is provided at its upper end with a bearing 146, at which a guide or link lever 145 is pivotably mounted about a horizontal pivot axis $A_4$. At the guide lever 145 there is hingedly connected at one side a thrust rod 135 and the other side is constructed for mounting a grippable arresting or locking element 150. The arresting element 150 comprises a bolt 149, preferably a threaded bolt, which can be inserted or threaded into the support arm or arm member 147 preferably reinforced with a bushing or sleeve 148 having an appropriately configured opening 148'. With the arresting element 150 inserted or threaded in the explained manner, the support arm 147 is operatively connected with the guide lever 145. Arranged laterally at the bearing 146 of the guide lever 145 is a brake bearing $B_4$, in which there is rotatably mounted in axial direction the support arm 147 about a lengthwise axis $A_6$. At the end of the support arm 147 there is provided a further brake bearing $B_5$ arranged transversely with respect to the brake bearing $B_4$, as best seen by referring to FIGS. 1 and 2.

As will be apparent from the showing of FIG. 1, the hinge parallelogram 155 composed of the hingedly interconnected parallelogram elements 155', is hingedly connected by means of one of the parallelogram elements at the support arm 147 and with another one of the parallelogram elements at the brake bearing $B_5$. Both of the other essentially horizontally oriented and mutually parallel extending parallelogram elements 155' of the parallelogram 150 are provided at their ends with a respective hinge element, generally designated by reference character 250, which are interconnected by a web or link 184. At the web or link 184 there is secured a further brake bearing $B_6$, a head element 185 which is rotatably mounted in the not-particularly referenced housing of the brake bearing $B_6$ and a coupling element 190 which is pivotably mounted in the housing 185' of the head element or piece 185. The coupling element 190 is constructed for the attachment of the schematically illustrated surgical microscope 160.

The parallelogram 155 with the brake bearing $B_6$, and the components 184, 185, 190 and 160 are rotatable by means of the elements hingedly connected at the support arm 147, about the axis of rotataion $A_6$ of the support arm 147 in the double-headed direction of the arrow $P_3$ and is pivotable about the axis $A_5$, arranged transversely with respect to the axis $A_6$, in the direction of the double-headed arrow $P_4$ and can be braked by means of the operatively associated brake bearings $B_4$ and $B_5$. The surgical microscope 160, hingedly connected at the coupling element 190, is additionally rotatable about the axis $A_7$ in the direction of the arrow $P_5$ and can be braked by the brake bearing $B_6$.

Figure 2:
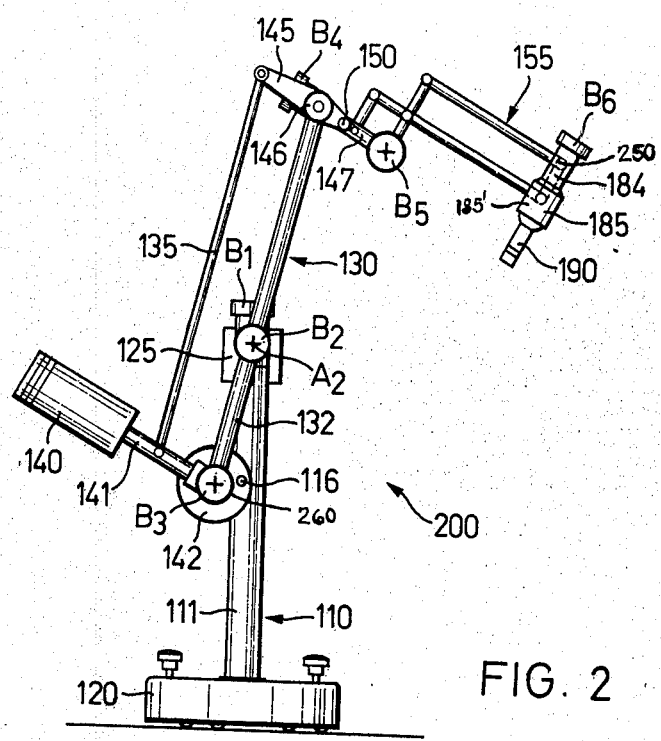
FIG. 2 illustrates details of the stand shown in FIG. 1, wherein however there have been essentially arrested or locked the pivotal arm at the stand column or upright and the guide lever at the support arm.

Now in FIG. 2 the stand 200 has been illustrated for instance for mounting purposes or for exchange of the microscope which has not been particularly shown in FIG. 2, in an arrested position, and further, there will be recognized the pivotal arm 130 which is arrested at the column body 111 and the support arm 147 with the hingedly connected parallelogram 155. The support arm 147 is arrested or locked at the guide lever 145 by the arresting or locking element 150.

At the lower region of the pivotal arm 130 there is arranged at the partial element 132 a brake bearing $B_2$ and a weight or weighting disk 142. At the housing 260 of the brake bearing $B_3$ there is additionally attached a rod 141 for receiving a counterweight 140. The rod or rod member 141, carrying the counterweight 140 as well as the guide lever 145 hingedly connected at the upper end of the pivotal arm or arm member 130, are operatively connected by the thrust rod 135. This thrust rod 135 extends essentially parallel to the pivotal arm 130 and is hingedly connected with the rod member or rod 141 and with the guide lever 145. The pivotal movements, as indicated by the arrows $P_2$, $P_2'$ of the arm member 130 bring about a pivotal movement of the lever 145 about the horizontal axis $A_4$ of the bearing 146 and the rod 141 with the counterweight 140 about the horizontal axis $A_3$ of the brake bearing $B_3$, so that the guide lever 145 together with the rod 141 and the thrust rod 145 together with the pivotal arm 130 extensively extend in parallelism to one another in each position.

Figure 6:
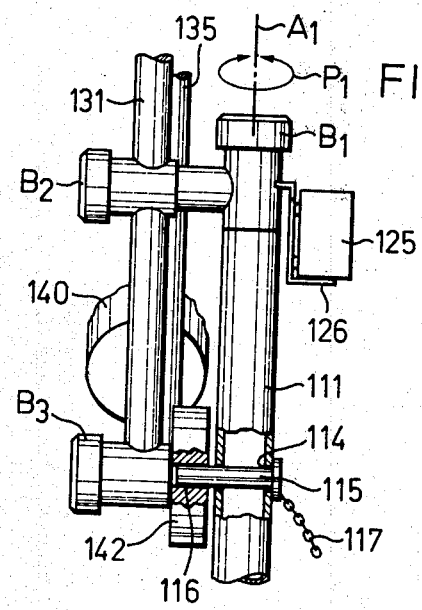
FIG. 6 is a fragmentary sectional side view showing in detail the arresting of the pivotal arm of the arrangement of FIG. 5.
Figure 5:
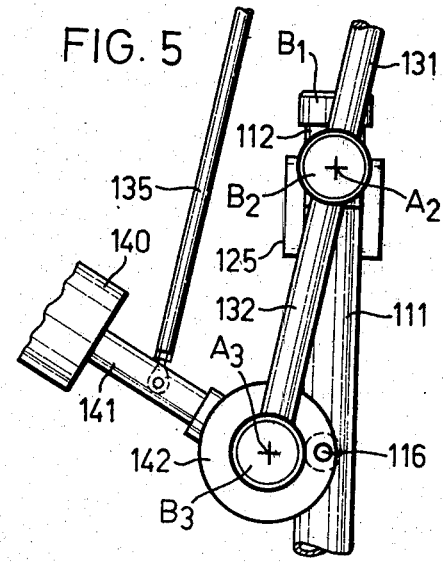
FIG. 5 is a fragmentary enlarged view of the pivotal arm which has been locked or arrested at the column body of the stand column.

At the head element or piece 112 there is attached at the periphery and offset with respect to the brake bearing $B_2$ an angle member or element 126, serving for receiving an instrument cabinet 125 for the power supply of the microscope 160 (FIGS. 5 and 6).

In FIG. 5 there has been shown in front view and in FIG. 6 in side view and partially in sectional view, on an enlarged scale, the arresting or locking of the complete pivotal arm or arm member 130 at the column body 111, this arm member 130, as will be recalled, comprising the partial elements 131, 132. Also, there will be seen the brake bearing $B_3$ arranged at the partial element 132, the weight disk 142, the rod 141 and the counterweight 140. The partial element 132 together with the weight disk 142 and the counterweight 140 is shown in FIG. 6 to be movable laterally about the horizontal axis $A_2$ past the column body 111, this pivotal movement being braked by the brake bearing $B_2$. The weight disk 142 possesses at least one opening 116 arranged at the outer circumference of the disk 142 and the column body 111 possesses an opening 114 which radially pierces through such column body. As soon as during the pivotal movement both of the openings 116, 114 are in alignment with one another, then it is possible to insert an arresting or locking bolt 115, attached at the column body 111 by means of a chain 117 or equivalent structure, through the opening 114 of the column body 111 into the opening 116 of the weight or weighting disk 142, whereby the partial element 132 of the pivotal arm 130, as illustrated in FIG. 6, is arrested at the column body 111.

The parallel movement of the guide lever 145 with respect to the rod 141 together with the counterweight 140 is adjustable and controllable by means of the brake bearing $B_3$.

The bearings $B_1$, $B_2$, $B_3$, $B_4$, $B_5$ and $B_6$, arranged at the corresponding hinge location of the stand 200, are constructed as conventional rotary and brake bearings and each individual brake bearing can be manually adjusted, so that the brake force which is effective at the rotary and/or pivotal movement of the individual support and pivotal elements, can be randomly accommodated and adjusted to the prevailing requirements.

While there are shown and described present preferred embodiments of the invention it is to be distinctly understood that the invention is not limited thereto but may be otherwise variously embodied and practised within the scope of the following claims. Accordingly,

What we claim is:

1. An arrangement at a stand for an optical observation device, comprising:
    a stand column;
    a pivotal arm mounted at said stand column;
    a counterweight provided for said pivotal arm;
    a support arm cooperating with said pivotal arm;
    hinge parallelogram means cooperating with said support arm;
    a plurality of rotary and brake bearings provided for said stand;
    said hinge parallelogram means being structured at its front region for receiving an optical observation device;
    said pivotal arm having opposed ends;
    a guide lever pivotably mounted at one end of the pivotal arm for pivotable movement about a first horizontal axis;
    a weight disk arranged at the other end of the pivotal arm at a second horizontal axis;
    one of said rotary and brake bearings being arranged at the other end of said pivotal arm at said second horizontal axis;
    a rod member secured to said one brake bearing;
    said rod member supporting said counterweight;
    said rod member extending transversely with respect to said second horizontal axis and essentially parallel to said guide lever;
    a thrust rod for operatively connecting said rod member with said guide lever; and
    said thrust rod extending essentially parallel to said pivotal arm.

2. The arrangement as defined in claim 1, further including:
    means for fixedly adjusting said support arm at said guide lever;
    said pivotal arm being formed of two partial elements;
    said stand column comprising a column body member; and
    means for fixedly adjusting said pivotal arm together with said weight disk at the column body of said stand column.

3. The arrangement as defined in claim 2, further including:
    arresting means provided for said guide lever;
    said arresting means comprising a bolt member; and
    said support arm having an opening for receiving said bolt member of said arresting means.

4. The arrangement as defined in claim 2, wherein:
    said column body contains a radially piercing opening;
    said weight disk containing an opening; and
    both of said openings being in alignment with one another in a certain position of the pivoted support arm.

5. The arrangement as defined in claim 4, further including:
    bolt means piercingly extendible through the opening of the column body in order to fixedly adjust the pivotal arm together with the weight disk at the stand column.

6. The arrangement as defined in claim 1, further including:
    means for fixedly adjusting said support arm at said guide lever;
    means for fixedly adjusting said pivotal arm together with said weight disc at said stand column, whereby said pivotal arm and said hinge parallelogram means can be selectively fixedly positioned in a mounting position and dismantling position for the optical observation device.

* * * * *